US010624909B2

(12) United States Patent
Ivarsson et al.

(10) Patent No.: US 10,624,909 B2
(45) Date of Patent: Apr. 21, 2020

(54) INOSITOL DERIVATIVES FOR USE IN PATHOLOGICAL CRYSTALLIZATION

(71) Applicants: ETH Zurich, Zurich (CH); UNIVERSITAT BERN, Bern (CH)

(72) Inventors: Mattias Ivarsson, Zurich (CH); Bastien Castagner, Montreal (CA); Jean-Christophe Leroux, Zurich (CH); Andreas Pasch, Bern (CH)

(73) Assignees: ETH ZURICH, Zurich (CH); UNIVERSITAT BERN, Bern (CH)

( * ) Notice: Subject to any disclaimer, the term of this patent is extended or adjusted under 35 U.S.C. 154(b) by 0 days.

(21) Appl. No.: 16/060,980

(22) PCT Filed: Dec. 12, 2016

(86) PCT No.: PCT/EP2016/080657
§ 371 (c)(1),
(2) Date: Jun. 11, 2018

(87) PCT Pub. No.: WO2017/098047
PCT Pub. Date: Jun. 15, 2017

(65) Prior Publication Data
US 2019/0175627 A1    Jun. 13, 2019

(30) Foreign Application Priority Data

Dec. 11, 2015 (EP) ..................... 15199682
Apr. 7, 2016 (EP) ..................... 16164299
Jun. 7, 2016 (EP) ..................... 16173422

(51) Int. Cl.
| | | |
|---|---|---|
| *A61K 31/6615* | (2006.01) | |
| *A61K 47/60* | (2017.01) | |
| *A61P 9/10* | (2006.01) | |
| *A61P 13/12* | (2006.01) | |
| *A61P 9/14* | (2006.01) | |

(52) U.S. Cl.
CPC .......... *A61K 31/6615* (2013.01); *A61K 47/60* (2017.08); *A61P 9/10* (2018.01); *A61P 9/14* (2018.01); *A61P 13/12* (2018.01)

(58) Field of Classification Search
None
See application file for complete search history.

(56) References Cited

U.S. PATENT DOCUMENTS

2014/0271915 A1    9/2014  Perello Bestard et al.

FOREIGN PATENT DOCUMENTS

| | | |
|---|---|---|
| EP | 0269105 | 6/1988 |
| EP | 2022501 | 2/2009 |
| EP | 2324835 | 5/2011 |
| WO | 2010018278 | 2/2010 |
| WO | 2013045107 | 4/2013 |

OTHER PUBLICATIONS

Grases F et al: "Phytate (IP6) is a Prowerful Agent for Preventing Calcifications in Biological Fluids: Usefulness in Renal Lithiasis Treatment", Anticancer Research—International Journal of Cancer Research and Treatment, International Institute of Anticancer Reasearch, GR, vol. 19, No. 5A, Jan. 1, 1999, pp. 3717-3722.
Neil S. Keddie et al: "Development of inositol-based antagonists for the D-myo-inositol 1,4,5-trisphosphate receptor", Chemical Communications-Chemcom., vol. 47, No. 1, Jan. 1, 2011, pp. 242-244.
Elisabeth V. Giger et al: "siRNA Transfection with Calcium Phosphate Nanoparticles Stabilized with PEGylated Chelators", Advanced Healthcare Materials, vol. 2, No. 1, Jan. 1, 2013, pp. 134-144.
Felix Grases et al: "Phytate (Myo-inositol hexakisphosphate) inhibits cardiovascular calcifications in rats", Frontiers in Bioscience, vol. 11, No. 1, Jan. 1, 2006, pp. 136-142.
Mattheolabakis G et al: "Pegylation improves the pharmacokinetics and bioavailability of small-molecule drugs hydrolyzable by esterases: A study of phosph-ibuprofen", Journal of Pharmacology and Experimental Therapeutics 2014101 American Society for Pharmacology and Experimental Therapy USA, vol. 351, No. 1 Oct. 2014, pp. 61-66.
Bailon, P. and Won, C. (2009). PEG-modified biopharmaceuticals. Expert Opin. Drug Deliv., 6(1).
Veronese, F. and Pasut, G. (2005). PEGylation, successful approach to drug delivery. Drug Discovery Today, 10(21).
Zhang, X., Wang, H., Ma, Z. and Wu, B. (2014). Effects of pharmaceutical PEGylation on drug metabolism and its clinical concerns. Expert Opinion on Drug Metabolism & Toxicology, 10(12), p. 1.
Weinhart, M., Grunwald, I., Wyszogrodzka, M., Gaetjen, L., Hartwig, A. and Haag, R. (2010). Linear Poly (methylglycerol) and Linear Polyglycerol as Potent Protein and Cell Resistant Alternatives to Poly(ethylene glycol). Chemistry, 5, p. 1993.

*Primary Examiner* — Samantha L Shterengarts
(74) *Attorney, Agent, or Firm* — JMB Davis Ben-David (57) ABSTRACT

The present invention relates to inositol derivatives covalently modified with one, two or three solubility functions, particularly polyethylene glycol moieties, for use in therapy or prevention of conditions related to pathological calcium crystallization, such as cardiovascular calcifications, nephrocalcinosis, calcinosis cutis, chondrocalcinosis and kidney stones.

20 Claims, 1 Drawing Sheet

INOSITOL DERIVATIVES FOR USE IN PATHOLOGICAL CRYSTALLIZATION

CROSS-REFERENCE TO RELATED APPLICATIONS

This is the U.S. National Stage of International Patent Application No. PCT/EP2016/080657 filed on Dec. 12, 2016, which was published in English under PCT Article 21(2), and which in turn claims the priority of European Patent Application Nos. 15199682.4 filed Dec. 11, 2015, 16164299.6 filed Apr. 7, 2016, and 16173422.3 filed on Jun. 7, 2016.

The present invention relates to the use of pharmaceutical compounds for treating or preventing conditions related to pathological calcium crystallization.

BACKGROUND OF THE INVENTION

Patients with chronic kidney disease (CKD) suffer from accelerated mineral deposition in soft tissues, in particular in the vascular system, due to a loss in homeostasis of factors that regulate biomineralization processes in the body. Such deposits lead to stiffening of arterial walls, which ultimately leads to increased blood pressure, left ventricular hypertrophy, reduced coronary blood flow, compromised endothelial function and damage to the microcirculation in the kidneys and brain. As a result, all-cause mortality of CKD patients increases exponentially as renal function decreases.

Physiological calcium and phosphate concentrations in the blood are close to supersaturation. Blood components such as fetuin-A interact with calcium and phosphate to form soluble nanoparticles termed calciprotein particles (CPPs) that prevent precipitation and resultant calcification under normal conditions. So-called primary CPPs are amorphous and have a hydrodynamic radius of typically less than 100 nm and mature with time to reorganize into crystalline secondary CPPs that have a hydrodynamic radius of more than 100 nm. Secondary CPPs are subsequently thought to progress to calcification and to initiate pathological responses.

A pharmaceutical agent capable of reducing the propensity for progression of primary CPPs to secondary CPPs, and hence ultimately capable of reducing pathological crystallization, would therefore be of significant therapeutic value. There is, to date, no approved or clinically validated therapy for the reduction or prevention of vascular calcifications.

Thus, the problem underlying the present invention is to provide an efficacious pharmacological intervention for reducing pathological crystallization. This problem is solved by the subject matter of the independent claims.

Description

The present invention relates to the use of inositol phosphates, sulfates, and/or thiophosphates with or without covalent addition of poly(ethylene glycol) (PEG) or polyglycerol, in preventing or reducing pathological crystallization in soft tissues.

According to a first aspect of the invention, a compound described by a general formula (I)

is provided for use in therapy or prevention of conditions related to pathological calcium crystallization, wherein
   Z is $(CHX)_p CHX(CHX)_q$;
   p and q each independently from the other have a value from 0 to 2, with the proviso that (p+q) has a value of 0, 1 or 2;
   one or two or three X can be $R^1$ and the remaining X independently from each other are selected from $OPO_3^{2-}$, $OPSO_2^{2-}$, and $OSO_3^-$, with the proviso that not all X are $OPO_3^{2-}$ and not all X are $OSO_3^-$; and
   $R^1$ comprises a solubility function $R^2$ selected from the group including
      a polyethylene glycol or
      a polyglycerol.

Conditions related to pathological calcium crystallization for which the compounds of the present invention are particularly useful include vascular calcification, coronary artery disease, vascular stiffening, valvular calcification, nephrocalcinosis, calcinosis cutis, kidney stones, chondrocalcinosis, osteoporosis, myocardial infarction, cardiovascular mortality (particularly in chronic kidney disease patients), progression of chronic kidney disease and failure of renal transplant grafts. Pathological crystallization has been shown to be associated with all-cause mortality of chronic kidney disease patients, hence the compounds of the present invention are indicated for chronic kidney disease patients in general.

Further conditions that will benefit from a treatment with the compounds of the invention are peripheral arterial disease, critical limb ischemia, calciphylaxis, general arterial calcification of infancy, aortic stenosis, atherosclerosis, pseudogout, primary hyperoxaluria and pseudoxanthoma elasticum.

In the context of the present specification, "peripheral arterial disease" refers to a narrowing of the peripheral arteries to the legs (most commonly), stomach, arms, and head. Symptoms include intermittent claudication (leg pain when walking which resolves with rest), skin ulcers, bluish skin, cold skin, or poor nail and hair growth.

In the context of the present specification, "critical limb ischemia" refers to a severe obstruction of the arteries which markedly reduces blood flow to the extremities, and progresses to the point of severe pain and even skin ulcers, sores, or gangrene. Critical limb ischemia is a very severe condition of peripheral artery disease.

In the context of the present specification, "calciphylaxis" or "calcific uremic arteriolopathy" relates to a syndrome of vascular calcification, thrombosis and skin necrosis.

In the context of the present specification, "pseudogout", also known as "Calcium pyrophosphate dihydrate (CPPD) crystal deposition disease" or "pyrophosphate arthropathy" relates to a rheumatologic disorder believed to be caused by calcium pyrophosphate crystal accumulation in connective tissues, particularly joints such as the knee joint.

In the context of the present specification, the term "general arterial calcification of infancy" (GACI) relates to a disorder affecting the circulatory system that becomes apparent before birth or within the first few months of life, and which is characterized by abnormal calcification of the arteries and thickening of the arterial walls. These changes lead to stenosis and stiffness of the arteries, resulting in heart failure in some affected individuals, with signs and symptoms including difficulty breathing, edema, cyanosis, hypertension and cardiomegaly.

Some degree of flexibility exists as to the optimal composition of the anionic binding moiety as well as that of the polymeric solubility function. Without wanting to be bound by theory, the inventors hypothesize that this is due to the fact that the interactions that provide the therapeutic benefit mainly consist of electrostatic interactions between small anions and cations in combination with steric hindrance, and both phenomena are, in terms of requirement of fit of molecular interaction, less selective than e.g. a protein-ligand interaction.

In certain embodiments, $R^1$ is $R^2$ and the compound is used for treatment of any of the indications listed above.

In certain embodiments, $R^1$ is or comprises a polyethylene glycol or a polyglycerol, and $R^1$ has a molar mass between 100 g/mol and 3000 g/mol, particularly between 100 g/mol and 2500 g/mol, more particularly of approx. 100 g/mol to 2000 g/mol, and the compound is used for treatment of any of the indications listed above.

In certain embodiments, $R^1$ is or comprises a polyethylene glycol or a polyglycerol, and $R^1$ has a molar mass between 200 g/mol and 3000 g/mol, particularly between 300 g/mol and 2500 g/mol, more particularly of approx. 400 g/mol to 2000 g/mol, and the compound is used for treatment of any of the indications listed above.

In certain embodiments, the compound is described by a general formula (II)

(II)

wherein
one or two or three X are $R^1$ and the remaining X independently from any other X can be $OPO_3^{2-}$, $OPSO_2^{2-}$, and $OSO_3^-$ and
$R^1$ is a polyethylene glycol or a polyglycerol;
and the compound is used for treatment of any of the indications listed above.

The straight lines in formula II are meant to indicate that the stereochemistry of the individual ring carbon atoms is undefined. The formula is meant to encompass any diastereomer.

In certain embodiments, $R^1$ is a polyethylene glycol.

In certain embodiments, $R^1$ is a polyethylene glycol described by a formula $R^3$—$(O-CH_2-CH_2)_n$— or $R^3$—$(O-CH_2-CH_2)_n$—O— and $R^3$ is hydrogen, methyl or ethyl, and n has a value from 2 to 200.

In certain embodiments, n has a value from 3 to 200.

In certain embodiments, n has a value from 3 to 20. In certain embodiments, n has a value from 10 to 30. In certain embodiments, n has a value from 9 to 45.

In certain embodiments, n has a value from 7 to 11.

In certain embodiments, n has a value of 2. In certain embodiments, n has a value of 7. In certain embodiments, n has a value of 9. In certain embodiments, n has a value of 11. In certain embodiments, n has a value of 45.

In certain embodiments, the compound is described by the general formula (II), one X is $R^1$ and the remaining X independently from any other X can be $OPO_3^{2-}$, $OPSO_2^{2-}$, and $OSO_3^-$; and $R^1$ is a polyethylene glycol or a polyglycerol having a molar mass between 100 g/mol and 3000 g/mol, particularly between 100 g/mol and 2500 g/mol, more particularly of approx. 100 g/mol to 2000 g/mol, and the compound is used for treatment of any of the indications listed above.

In certain embodiments, the compound is described by the general formula (II), one X is $R^1$ and the remaining X independently from any other X can be $OPO_3^{2-}$, $OPSO_2^{2-}$, and $OSO_3^-$; and $R^1$ is a polyethylene glycol or a polyglycerol having a molar mass between 200 g/mol and 3000 g/mol, particularly between 300 g/mol and 2500 g/mol, more particularly of approx. 400 g/mol to 2000 g/mol, and the compound is used for treatment of any of the indications listed above.

In certain embodiments, the compound is described by the general formula (II), wherein
one X is $R^1$ and the remaining X are $OPO_3^{2-}$; and
$R^1$ is a polyethylene glycol and has a molar mass between 100 g/mol and 3000 g/mol, particularly between 100 g/mol and 2500 g/mol, more particularly of approx. 100 g/mol or of approx. 2000 g/mol;
and the compound is used for treatment of any of the indications listed above.

In certain embodiments, the compound is described by the general formula (II), wherein
one X is $R^1$ and the remaining X are $OPO_3^{2-}$; and
$R^1$ is a polyethylene glycol and has a molar mass between 200 g/mol and 3000 g/mol, particularly between 300 g/mol and 2500 g/mol, more particularly of approx. 400 g/mol or of approx. 2000 g/mol;
and the compound is used for treatment of any of the indications listed above.

In certain embodiments, the compound is described by the general formula (II) and
two X are $R^1$ and the remaining X independently from any other X can be $OPO_3^{2-}$, $OPSO_2^{2-}$, and $OSO_3^-$; and
each $R^1$ independently from the other is selected from a polyethylene glycol and a polyglycerol;
and the compound is used for treatment of any of the indications listed above.

In certain embodiments, the compound is described by the general formula (II), two X are $R^1$ and the remaining X independently from any other X can be $OPO_3^{2-}$, $OPSO_2^{2-}$, and $OSO_3^-$; and each $R^1$ independently from the other is a polyethylene glycol or a polyglycerol having a molar mass between 100 g/mol and 3000 g/mol, particularly between 100 g/mol and 2500 g/mol, more particularly of approx. 100 g/mol to 2000 g/mol, and the compound is used for treatment of any of the indications listed above.

In certain embodiments, the compound is described by the general formula (II), two X are $R^1$ and the remaining X independently from any other X can be $OPO_3^{2-}$, $OPSO_2^{2-}$, and $OSO_3^-$; and each $R^1$ independently from the other is a polyethylene glycol or a polyglycerol having a molar mass between 200 g/mol and 3000 g/mol, particularly between 300 g/mol and 2500 g/mol, more particularly of approx. 400 g/mol to 2000 g/mol, and the compound is used for treatment of any of the indications listed above.

In certain embodiments, the compound is described by the general formula (II), wherein
two X are $R^1$ and the remaining X are $OPO_3^{2-}$; and
$R^1$ is a polyethylene glycol and has a molar mass
between 100 g/mol and 3000 g/mol, particularly between 100 g/mol and 2500 g/mol, more particularly of approx. 100 g/mol or of approx. 2000 g/mol
or
between 200 g/mol and 3000 g/mol, particularly between 300 g/mol and 2500 g/mol, more particularly of approx. 400 g/mol or of approx. 2000 g/mol;
and the compound is used for treatment of any of the indications listed above.

In certain embodiments, the compound is described by the general formula (II), wherein
two X are $R^1$ and the remaining X are $OPSO_2^{2-}$; and
$R^1$ is a polyethylene glycol and has a molar mass
between 100 g/mol and 3000 g/mol, particularly between 100 g/mol and 2500 g/mol, more particularly of approx. 100 g/mol or of approx. 2000 g/mol
or
between 200 g/mol and 3000 g/mol, particularly between 300 g/mol and 2500 g/mol, more particularly of approx. 400 g/mol or of approx. 2000 g/mol;
and the compound is used for treatment of any of the indications listed above.

In certain embodiments, the compound is described by the general formula (II), wherein
two X are $R^1$ and the remaining X are $OSO_3^-$; and
$R^1$ is a polyethylene glycol and has a molar mass
between 100 g/mol and 3000 g/mol, particularly between 100 g/mol and 2500 g/mol, more particularly of approx. 100 g/mol or of approx. 2000 g/mol
or
between 200 g/mol and 3000 g/mol, particularly between 300 g/mol and 2500 g/mol, more particularly of approx. 400 g/mol or of approx. 2000 g/mol;
and the compound is used for treatment of any of the indications listed above.

In certain embodiments, the compound is described by the general formula (II) and
three X are $R^1$ and the remaining X independently from any other X can be $OPO_3^{2-}$, $OPSO_2^{2-}$, and $OSO_3^-$; and
each $R^1$ independently from the other is selected from a polyethylene glycol and a polyglycerol;
and the compound is used for treatment of any of the indications listed above.

In certain embodiments, the compound is described by the general formula (II), three X are $R^1$ and the remaining X independently from any other X can be $OPO_3^{2-}$, $OPSO_2^{2-}$, and $OSO_3^-$; and each $R^1$ independently from the other is a polyethylene glycol or a polyglycerol having a molar mass
between 100 g/mol and 3000 g/mol, particularly between 100 g/mol and 2500 g/mol, more particularly of approx. 100 g/mol to 2000 g/mol, or
between 200 g/mol and 3000 g/mol, particularly between 300 g/mol and 2500 g/mol, more particularly of approx. 400 g/mol to 2000 g/mol;
and the compound is used for treatment of any of the indications listed above.

In certain embodiments, the compound is described by the general formula (II), wherein
three X are $R^1$ and the remaining X are $OPO_3^{2-}$; and
$R^1$ is a polyethylene glycol and has a molar mass
between 100 g/mol and 3000 g/mol, particularly between 100 g/mol and 2500 g/mol, more particularly of approx. 100 g/mol or of approx. 2000 g/mol
or
between 200 g/mol and 3000 g/mol, particularly between 300 g/mol and 2500 g/mol, more particularly of approx. 400 g/mol or of approx. 2000 g/mol;
and the compound is used for treatment of any of the indications listed above.

In certain embodiments, the compound is described by the general formula (II), wherein
three X are $R^1$ and the remaining X are $OPSO_2^{2-}$; and
$R^1$ is a polyethylene glycol and has a molar mass
between 100 g/mol and 3000 g/mol, particularly between 100 g/mol and 2500 g/mol, more particularly of approx. 100 g/mol or of approx. 2000 g/mol
or
between 200 g/mol and 3000 g/mol, particularly between 300 g/mol and 2500 g/mol, more particularly of approx. 400 g/mol or of approx. 2000 g/mol;
and the compound is used for treatment of any of the indications listed above.

In certain embodiments, the compound is described by the general formula (II), wherein
three X are $R^1$ and the remaining X are $OSO_3^-$; and
$R^1$ is a polyethylene glycol and has a molar mass
between 100 g/mol and 3000 g/mol, particularly between 100 g/mol and 2500 g/mol, more particularly of approx. 100 g/mol or of approx. 2000 g/mol
or
between 200 g/mol and 3000 g/mol, particularly between 300 g/mol and 2500 g/mol, more particularly of approx. 400 g/mol or of approx. 2000 g/mol;
and the compound is used for treatment of any of the indications listed above.

In certain embodiments, the compound is characterized by a general formula (III a), (III b), (III c) or (III d):

(III a)

(III b)

(III c)

-continued (III d)

wherein each X (independently) and $R^1$ have the meaning outlined above and the compound is used for treatment of any of the indications listed above.

In certain embodiments, the compound is characterized by a general formula (III e), (III f), (III g), (III h), (III i) or (III j):

(III e)

(III f)

(III g)

(III h)

(III i)

(III j)

wherein $R^1$ has the meaning outlined above and the compound is used for treatment of any of the indications listed above.

In certain embodiments, more than one $R^1$ is present and each $R^1$ is the same as any other $R^1$.

In certain embodiments, the compound is characterized by a general formula (IV a), (IV b), (IV c), (IV d), (V a) or (V b)

(IV a)

(IV b)

(IV c)

(IV d)

(V a)

(V b)

wherein each X (independently) and $R^1$ have the meaning outlined above and the compound is used for treatment of any of the indications listed above.

In certain embodiments, one or two or three X are $R^1$ and the remaining X are
- all $OPO_3^{2-}$ or
- all $OPSO_2^{2-}$ or
- all $OSO_3^{-}$.

In certain embodiments,
one or two or three X are $R^1$ and the remaining X are $OPO_3^{2-}$; and
$R^1$ is a polyethylene glycol and has a molar mass between 100 g/mol and 3000 g/mol, particularly between 100 g/mol and 2500 g/mol, more particularly of approx. 100 g/mol or of approx. 2000 g/mol.

In certain embodiments,
one or two or three X are $R^1$ and the remaining X are $OPSO_2^{2-}$; and
$R^1$ is a polyethylene glycol and has a molar mass between 100 g/mol and 3000 g/mol, particularly between 100 g/mol and 2500 g/mol, more particularly of approx. 100 g/mol or of approx. 2000 g/mol.

In certain embodiments, three X are $R^1$.

In certain embodiments, one X is $R^1$ and of the remaining X
three X are $OSO_3^-$ and two X are $OPSO_2^{2-}$, or three X are $OSO_3^-$ and two X are $OPO_3^{2-}$, and
$R^1$ is a polyethylene glycol and has a molar mass between 100 g/mol and 3000 g/mol, particularly between 100 g/mol and 2500 g/mol, more particularly of approx. 100 g/mol or of approx. 2000 g/mol.

In certain embodiments, $R^1$ is or comprises a polyethylene glycol characterized by a formula $R^3$—(O—$CH_2$—$CH_2$)$_n$— or $R^3$—(O—$CH_2$—$CH_2$)$_n$—O— and $R^3$ is hydrogen, methyl or ethyl.

In certain embodiments, the compound is described by a general formula (III k), (III l), (III m) or (III n)

wherein n has a value from 2 to 200. In certain embodiments, n is 2 or n is 7 to 50. In certain embodiments, n is 2, 7 to 12 or 40 to 50. In certain embodiments, n is 2, 7, 9, 11 or 45. The compound is used for treatment of any of the indications listed above.

In certain embodiments, the compound is described by a general formula (III k), (III l), (III m) or (III n), wherein n has a value from 3 to 200, particularly 7 to 50, more particularly 7 to 12 or 40 to 50, even more particularly 9 or 45, and the compound is used for treatment of any of the indications listed above.

In certain embodiments, the compound is described by any one of formulae (III o), (III p), (III q), (III r), (III s), (III t), (III u), (III v), (III w), (III x), (III y) or (III z)

-continued and the compound is used for treatment of any of the indications listed above.

With regard to the substituents ($OPO_3^{2-}$, $OPSO_2^{2-}$, $OSO_3^-$) and the length of the PEG moieties, formula (III m) with n=2 corresponds to formula (III o)/compound INS-2001;
formula (III m) with n=7 corresponds to formula (III p)/compound INS-2031;
formula (III m) with n=11 corresponds to formula (III q)/compound INS-2041;
formula (III n) with n=2 corresponds to formula (III u)/compound INS-4001;
formula (III n) with n=7 corresponds to formula (III v)/compound INS-4031; and
formula (III n) with n=11 corresponds to formula (III w)/compound INS-4041.

In certain embodiments, the compound is described by a general formula (IV e) or (V c)

wherein n has a value from 2 to 200, particularly 2 or 7 to 50, more particularly 2, 7 to 12 or 40 to 50, even more particularly 2, 7, 9, 11 or 45, and the compound is used for treatment of any of the indications listed above.

Figure 1:
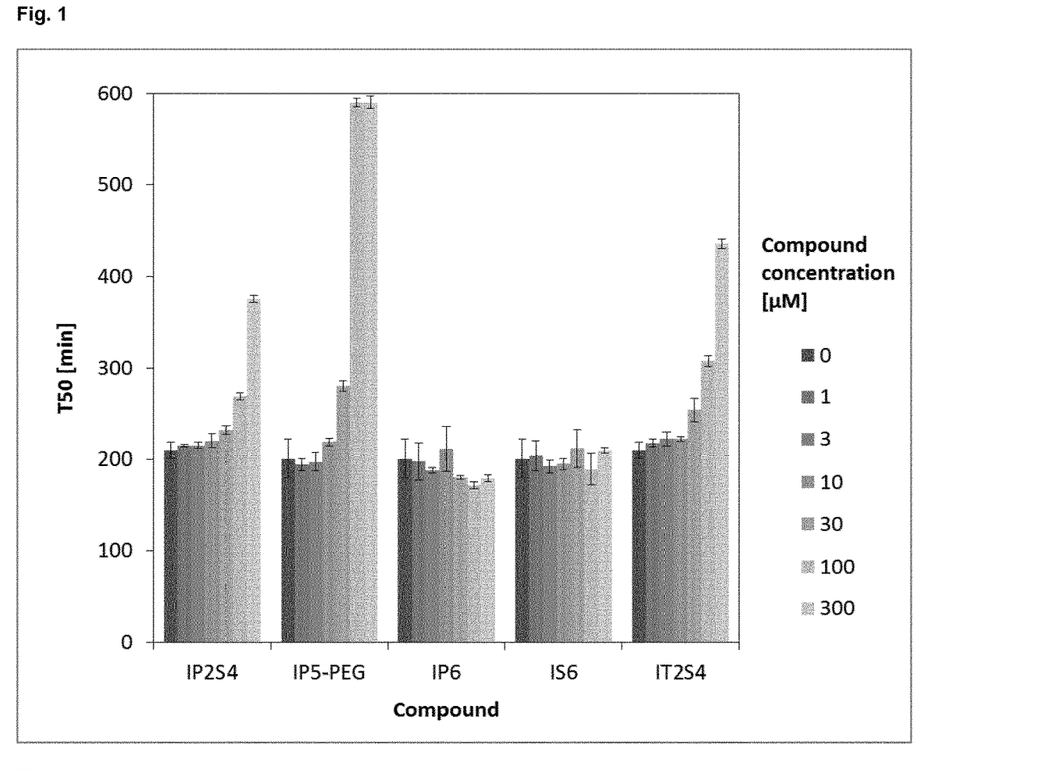
FIG. 1 shows calciprotein particle (CPP) maturation time in human serum according to the test described in Pasch et al. JASN 2012. The y-axis indicates the half-maximal transition time ($T_{50}$) in minutes of primary CPPs to secondary CPPs. IP6: myo-inositol hexakisphosphate (Biosynth); IS6: myo-inositol hexakissulfate (Sigma); IP2S4: 4,6-di-(O-phosphate)-myo-inositol 1,2,3,5-tetra-O-sulfate; IT2S4: 4,6-di-(O-thiophosphate)-myo-inositol 1,2,3,5-tetra-O-sulfate; IP5-PEG: 2-PEG(2000)-myo-inositol pentakisphosphate.

One embodiment of the invention that shows a particularly high activity is the use of 2-PEG-IP5 (myo-pentakis-inositolphosphate-(2)-PEG, specified by formula (IV e) with PEG moieties having a molar mass of approximately 400 g/mol (n=9) or approximately 2000 g/mol (n=45) for the indications listed above. This conclusion is drawn from the results of an in vitro assay that measures the propensity for calcification of human serum, which has been clinically validated as a predictor of all-cause mortality in CKD patients and renal transplant patients (FIG. 1). The inventors show that surprisingly, IP5-PEG is a much more potent inhibitor than IP6 in reducing the propensity for calcification of human serum. The result is unexpected because the removal of a phosphate group is presumed to reduce the molecule's affinity for calcium but this is evidently more than compensated for by the addition of the PEG moiety. Without wanting to be bound by theory, the inventors hypothesize that this is due to the fact that the PEG moiety increases the solubility of CPP complexes and provides steric hindrance that prevents the transformation from amorphous to crystalline calcium phosphate and/or crystal growth. Furthermore, adding a PEG (or another polymer) moiety to the molecule offers the possibility to tailor its circulation time and hence offers more flexible dosing schedules than IP6. This aspect has not been considered for IP6 analogues previously and presents a competitive advantage over IP6 for the present indication.

In certain embodiments, the compound is described by any one of formulae (IV f), (IV g), (IV h), (IV i), (IV j), (IV k), (V d), (V e), (V f), (V g), (V h) or (V i)

-continued

With regard to the substituents ($OPO_3^{2-}$, $OPSO_2^{2-}$, $OSO_3^-$) and the length of the PEG moieties, formula (IV e) with n=2 corresponds to formula (IV f)/compound INS-3001;
formula (IV e) with n=7 corresponds to formula (IV g)/compound INS-3031;
formula (IV e) with n=11 corresponds to formula (IV h)/compound INS-3041;
formula (V c) with n=2 corresponds to formula (V d)/compound INS-5001;
formula (V c) with n=7 corresponds to formula (V e)/compound INS-5031; and
formula (V c) with n=11 corresponds to formula (V f)/compound INS-5041.

In certain embodiments, wherever a polyethylene glycol chain is shown as a formula in the present specification, the PEG moiety is a monodisperse polyethylene glycol. In certain formulae, a monodisperse PEG moiety is assigned the abbreviation mdPEG.

In certain embodiments, the compound is described by a general formula (III o), (III p), (III q), (III u), (III v) or (III w)

In certain embodiments, a) (p+q) is 0, two out of five X are independently selected from $OPO_3^{2-}$ and $OPSO_2^{2-}$ and the remaining X are $OSO_3^-$, or
b) (p+q) is 0, three out of five X are independently selected from $OPO_3^{2-}$ and $OPSO_2^{2-}$ and the remaining X are $OSO_3^-$, or
c) (p+q) is 1, two out of six X are independently selected from $OPO_3^{2-}$ and $OPSO_2^{2-}$ and the remaining X are $OSO_3^-$, or
d) (p+q) is 1, three out of six X are independently selected from $OPO_3^{2-}$ and $OPSO_2^{2-}$ and the remaining X are $OSO_3^-$, or
e) (p+q) is 1, four out of six X are independently selected from $OPO_3^{2-}$ and $OPSO_2^{2-}$ and the remaining X are $OSO_3^-$, or f) (p+q) is 2, three out of seven X are independently selected from $OPO_3^{2-}$ and $OPSO_2^{2-}$ and the remaining X are $OSO_3^-$, or g) (p+q) is 2, four out of seven X are independently selected from $OPO_3^{2-}$ and $OPSO_2^{2-}$ and the remaining X are $OSO_3^-$ or h) (p+q) is 2, five out of seven X are independently selected from $OPO_3^{2-}$ and $OPSO_2^{2-}$ and the remaining X are $OSO_3^-$;

and the compound is used for treatment of any of the indications listed above.

In certain embodiments, the compound is described by formula

(VIa)

(VIb)

and is used for treatment of any of the indications listed above.

FIG. 1 demonstrates that this compound (4,6-di-(O-thiophosphate)-inositol-1,2,3,5-tetra-O-sulfate, IT2S4) is more active than IP6 in inhibiting the transition of primary to secondary CPPs and thus can reduce the propensity for calcification of human serum.

In certain embodiments, the compound is described by formula (VIc)

(VId)

and is used for treatment of any of the indications listed above.

FIG. 1 demonstrates that this compound (4,6-di-(O-phosphate)-inositol-1,2,3,5-tetra-O-sulfate, IP2S4) is more active than IP6 in inhibiting the transition of primary to secondary CPPs and thus can reduce the propensity for calcification of human serum.

According to a second aspect of the invention, a dosage form comprising the compound as specified by any of the above formulae is provided for use in therapy or prevention of conditions related to pathological calcium crystallization.

The dosage form may be formulated for parenteral administration, such as intravenous, intraperitoneal, intramuscular, intra-arterial or subcutaneous administration. Optionally, a pharmaceutically acceptable carrier and/or excipient may be present.

According to a third aspect of the invention, a dialysis solution for use in hemodialysis, hemofiltration or peritoneal dialysis comprising the compound as specified in the above aspects of the invention is provided for use in therapy or prevention of conditions related to pathological calcium crystallization.

According to another aspect of the invention, a method of treatment or prevention of any of the conditions related to pathological calcium crystallization listed above is provided, comprising the administration of the compound as specified by any of the above formulae to a subject in need thereof.

The compound may be administered intravenously, intraperitoneally, intramuscularly, intra-arterially or subcutaneously. Alternatively, the compound may be administered as a component of a haemodialysis or peritoneal dialysis solution.

Compound Claims

According to yet another aspect of the invention, a compound according to general formula (II) is provided, wherein two or three X are $R^1$ and the remaining X independently from other X are selected from $OPO_3^{2-}$, $OPSO_2^{2-}$ and $OSO_3^-$; and $R^1$ is a polyethylene glycol or a polyglycerol.

In certain embodiments of this aspect of the invention, two or three X are $R^1$ and the remaining X are
all OPO32- or
all OPSO22- or
all OSO3-.

In certain embodiments of this aspect of the invention, $R^1$ is a polyethylene glycol and has a molar mass between 100 g/mol and 3000 g/mol, particularly between 100 g/mol and 2500 g/mol, more particularly of approx. 100 g/mol to. 2000 g/mol.

Another aspect of the invention relates to a compound described by any one of formulae (IV a), (IV b), (IV c), (IV d), (V a) or (V b), wherein each X (independently) and $R^1$ have the meaning outlined above. In certain embodiments of this aspect of the invention, n (as part of the definition of $R^1$) has a value from 2 to 200. In certain embodiments of this aspect of the invention, n is 2 or n is 7 to 50. In certain embodiments of this aspect of the invention, n is 2, 7 to 12 or 40 to 50. In certain embodiments of this aspect of the invention, n is 2, 7, 9, 11 or 45.

In certain embodiments, the compound of the invention is described by any one of formulae (IV e) or (V c), and n has a value from 2 to 200. In certain embodiments of this aspect of the invention, n is 2 or n is 7 to 50. In certain embodiments of this aspect of the invention, n is 2, 7 to 12 or 40 to 50. In certain embodiments of this aspect of the invention, n is 2, 7, 9, 11 or 45.

In certain embodiments of this aspect of the invention, all X except the two or three X that are $R^1$ are phosphate.

In certain embodiments of this aspect of the invention, $R^1$ is a polyethylene glycol.

In certain embodiments of this aspect of the invention, $R^1$ has a molar mass between 100 g/mol and 3000 g/mol, particularly between 100 g/mol and 2500 g/mol, more particularly of approx. 100 g/mol to 2000 g/mol.

In certain embodiments of this aspect of the invention of this aspect of the invention, $R^1$ has a molar mass between 200 g/mol and 3000 g/mol, particularly between 300 g/mol and 2500 g/mol, more particularly of approx. 400 g/mol to 2000 g/mol.

Another aspect of the invention relates to a compound described by any one of formulae (IV f), (IV g), (IV h), (IV i), (IV j), (IV k), (V d), (V e), (V f), (V g), (V h) or (V i).

Any novel compound or compound group described herein is provided per se. It may be used advantageously as a medicament in the treatment of pathological crystallization and the specific medical uses provided herein.

The compound, dosage form or composition according to any one of the preceding claims for use in a condition related to pathological calcium crystallisation, wherein said condition is selected from vascular calcification, coronary artery disease, vascular stiffening, valvular calcification, nephrocalcinosis, calcinosis cutis, kidney stones, chondrocalcinosis, osteoporosis, myocardial infarction, cardiovascular mortality, progression of chronic kidney disease, failure of renal transplant grafts and peripheral arterial disease, critical limb ischemia, calciphylaxis, general arterial calcification of infancy and aortic stenosis, atherosclerosis, pseudogout, primary hyperoxaluria and pseudoxanthoma elasticum.

The compounds disclosed herein may be present in any form commonly used in pharmaceutical technology. Particular embodiments include, but are not limited to, the sodium salt, magnesium salt, potassium salt, ammonium salt, free acid, or a mixture of the preceding forms. Other pharmaceutically acceptable salts are known to the skilled artisan and can be obtained, inter alia, from Haynes et al., J. Pharmaceutical Sci. 94, 2005 2111-2120, DOI 10.1002/jps.20441

Terms and Definitions

In the context of the present specification, a monodisperse polyethylene glycol (mdPEG) is a PEG that has a single, defined chain length and molecular weight. mdPEGs are typically generated by separation from the polymerization mixture by chromatography.

Wherever alternatives for single separable features are laid out herein as "embodiments", it is to be understood that such alternatives may be combined freely to form discrete embodiments of the invention disclosed herein.

The invention is further illustrated by the following examples and figures, from which further embodiments and advantages can be drawn. These examples are meant to illustrate the invention but not to limit its scope.

EXAMPLES

TABLE 1

Compounds

| Compound | Formula | No. of PEG tails | $M_w$ of PEG (monodisperse) | $M_w$ of compound | Substituents other than PEG |
|---|---|---|---|---|---|
| INS-2001 | III o | 1 | 100 | 672.11 | 5 × $OPO_3^{2-}$ |
| INS-2031 | III p | 1 | 320 | 892.37 | 5 × $OPO_3^{2-}$ |
| INS-2041 | III q | 1 | 500 | 1068.59 | 5 × $OPO_3^{2-}$ |
| INS-2042 |  | 1 | 550 (polydisp.) | 1112.64 | 5 × $OPO_3^{2-}$ |
| INS-2101 | III r | 1 | 100 | 752.41 | 5 × $OPSO_2^{2-}$ |
| INS-2131 | III s | 1 | 320 | 972.68 | 5 × $OPSO_2^{2-}$ |
| INS-2141 | III t | 1 | 500 | 1148.89 | 5 × $OPSO_2^{2-}$ |
| INS-4001 | III u | 1 | 100 | 675.37 | 2 × $OPO_3^{2-}$, 3 × $OSO^{3-}$ |
| INS-4031 | III v | 1 | 320 | 895.63 | 2 × $OPO_3^{2-}$, 3 × $OSO^{3-}$ |
| INS-4041 | III w | 1 | 500 | 1071.84 | 2 × $OPO_3^{2-}$, 3 × $OSO^{3-}$ |
| INS-4101 | III x | 1 | 100 | 707.49 | 2 × $OPSO_2^{2-}$, 3 × $OSO^3$ |
| INS-4131 | III y | 1 | 320 | 927.75 | 2 × $OPSO_2^{2-}$, 3 × $OSO^3$ |
| INS-4141 | III z | 1 | 500 | 1103.96 | 2 × $OPSO_2^{2-}$, 3 × $OSO^3$ |
| INS-3001 | IV f | 2 | 100 | 696.28 | 4 × $OPO_3^{2-}$ |
| INS-3031 | IV g | 2 | 320 | 1136.81 | 4 × $OPO_3^{2-}$ |
| INS-3041 | IV h | 2 | 500 | 1489.23 | 4 × $OPO_3^{2-}$ |
| INS-3101 | IV i | 2 | 100 | 760.52 | 4 × $OPSO_2^{2-}$ |
| INS-3131 | IV j | 2 | 320 | 1201.05 | 4 × $OPSO_2^{2-}$ |
| INS-3141 | IV k | 2 | 500 | 1553.48 | 4 × $OPSO_2^{2-}$ |
| INS-5001 | V d | 3 | 100 | 720.45 | 3 × $OPO_3^{2-}$ |
| INS-5031 | V e | 3 | 320 | 1381.24 | 3 × $OPO_3^{2-}$ |
| INS-5041 | V f | 3 | 500 | 1909.88 | 3 × $OPO_3^{2-}$ |
| INS-5101 | V g | 3 | 100 | 768.63 | 3 × $OPSO_2^{2-}$ |
| INS-5131 | V h | 3 | 320 | 1429.42 | 3 × $OPSO_2^{2-}$ |
| INS-5141 | V i | 3 | 500 | 1958.06 | 3 × $OPSO_2^{2-}$ |

Calcification Assay

The inventors performed an in vitro assay that measures the propensity for calcification of human serum and has been clinically validated as a predictor of all-cause mortality in CKD patients and renal transplant recipients (as described in Pasch, Journal of the American Society of Nephrology 23, 1744-1752, 2012). The experiment was carried out by mixing a calcium solution, human pooled serum, the test compound at the final concentration indicated and a phosphate solution, and the transition time of primary to secondary CPPs was measured at 37° C. using a nephelometer for up to 600 minutes.

The data of FIG. 1 show that the compounds IP2S4 and IT2S4 are more active than IP6. Furthermore, compound 2-PEG-IP5 is far more active than any other compound in this assay. This result suggests a key role of the polymer moiety in preventing the transition of primary to secondary CPPs and in reducing the propensity for calcification of human serum.

Figure 2:
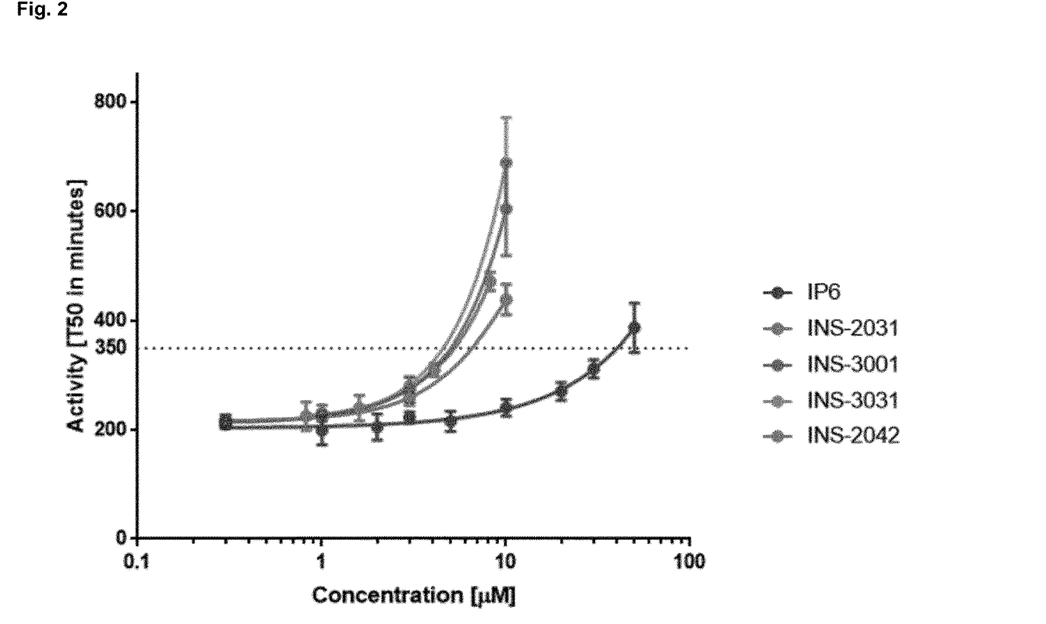
FIG. 2 shows the result of a determination of calciprotein particle (CPP) maturation time in human serum according to a similar test as in FIG. 1 (with the test compounds added to the reaction mixture last).

The data of FIG. 2 show that the compounds INS-2031 (III p), INS-3001 (IV f) and INS-3031 (IV g) are more active than IP6. The compounds having two PEG moieties (INS-3001, INS-3031) are more active than the compounds having one PEG moiety (INS-2031). This result suggests a key role of the polymer moiety in preventing the transition of primary to secondary CPPs and in reducing the propensity for calcification of human serum.

Synthesis of IT2S4 (VI a)

The synthesis followed the sequence depicted in the scheme below:

PTSA: p-toluenesulfonic acid;
DMF: dimethylformamide;
TBDMSCl: tert-butyldimethylsilyl chloride;
TBSO: tert-butyldimethylsilyl ether protection group;
DCM: dichloromethane;
S8: elemental sulphur;
pyr.: pyridine;
TMSBr: trimethylsilyl bromide;
TFA: trifluoroacetic acid Phosphorylation The known 2-tertbutyldimethylsilyl inositol orthoformate was co-evaporated 3× with toluene and dissolved in dichloromethane (DCM). 1H-tetrazole (4 eq.) followed by phosphoramidite (8 eq.) were added to the reaction and stirred overnight. Pyridine, followed by crushed sulphur flakes (20 eq.) were added to the reaction and stirred overnight. The resulting crude mixture was diluted with DCM and washed with saturated $NaHCO_3$, dried with $Na_2SO_4$, filtered and concentrated. The product was purified by flash chromatography with DCM in toluene.

$^1$H-NMR (400 MHz; CDCl3): δ 7.35-7.29 (m, 4H), 7.15 (dd, J=6.6, 2.1 Hz, 2H), 7.07-7.04 (m, 2H), 5.54 (d, J=1.1 Hz, 1H), 5.45-5.41 (m, 2H), 5.30-4.97 (m, 8H), 4.51-4.49 (m, 1H), 4.33-4.32 (m, 2H), 4.27 (d, J=1.3 Hz, 1H), 0.93 (s, 9H), 0.13 (s, 6H);

$^{31}$P-NMR (162 MHz; CDCl3): δ 70.1;

Deprotection

The following deprotection conditions are in analogy to the synthesis published in the Journal of the American Chemical Society (JACS 2005, 127, 5288).

Starting material (50 mg) was treated with thiophenol (300 μl), m-cresol (300 μl), trifluoroacetic acid (1.8 ml). Trimethylsilyl bromide (TMSBr) was then added slowly (360 μl). The mixture was stirred 2 h at room temperature. And then evaporated twice from toluene. The crude residue was diluted with DCM, and ca. 5 ml water and neutralized with 1N NaOH. The aqueous layer (slightly cloudy) was poured directly on SolEx C18 cartridge (Thermofisher, 1 g, 6 ml) and eluted with water. In some cases some aromatic impurities were found in the final product but would precipitate over time in water and could be filtered-off.

$^1$H-NMR (500 MHz; $D_2O$): δ 4.36 (q, J=9.6 Hz, 2H), 4.02 (t, J=2.7 Hz, 1H), 3.64 (dd, J=9.7, 2.8 Hz, 2H), 3.50 (t, J=9.3 Hz, 1H).

$^{31}$P-NMR (203 MHz; $D_2O$): δ 45.7

Sulfation

The sulfation reaction of the thiophosphate has to be performed carefully because the thiophosphate is eventually converted to the phosphate under the reaction conditions. We thus monitored the sulfation carefully and saw that the reaction was complete after ca. 30 min. and that no decomposition could be observed in this time. Thus, sulphurtrioxide dimethylformamide ($SO_3$-DMF) complex (12 eq.) was added to a suspension of inositol phosphate in DMF and the reaction was stirred 35 min. The reaction was quenched by adding 1N NaOH, until ca. pH 8 followed by ca. 3 ml methanol (MeOH) to precipitate salts. The solid was purified by Sephadex LH-20 column, eluting with water.

$^1$H-NMR (500 MHz; $D_2O$): δ 5.06 (s, 1H), 5.04-4.98 (m, 4H), 4.79-4.76 (m, 1H).

$^{31}$P-NMR (203 MHz; $D_2O$): δ 44.5

Synthesis of IP2S4 (VI c)

The synthesis followed the sequence depicted in the scheme below:

$^1$H-NMR (400 MHz, MeOD): δ (ppm)=4.40 (q, 3JHH=9.1 Hz, 2JHP=9.1 Hz, 2H, H—C4/6), 4.01 (t, J=2.6 Hz, 1H, H—C2), 3.63 (dd, J=9.68, 2.76 Hz, 2H, H—C1/3), 3.61 (t, J=9.27 Hz, 1H, H—C5);

$^{31}$P-NMR (160 MHz, 1H-decoupled, MeOD): δ (ppm)=1.15 (P—C4/6); 13CNMR (150 MHz, MeOD): δ (ppm)=81.28 (d, 2JCP=6.1 Hz, 2 C, C4/6), 74.12 (t, 3JCP=3.8, 1 C, C5), 73.75 (s, 1 C, C2), 72.13 (d, 3JCP=3.2 Hz, 2 C, C1/3); [m/z (ESI) (M+H)+C6H15O12P2 required 341.0033, found 341.0037].

PTSA: p-toluenesulfonic acid;
DMF: dimethylformamide;
TBDMSCl: tert-butyldimethylsilyl chloride;
TBDMSO: tert-butyldimethylsilyl ether protection group;
DCM: dichloromethane;
ACN: acetonitrile;
mCPBA: meta-chloroperoxybenzoic acid;
TMSBr: trimethylsilyl bromide;
$SO_3$—$Et_3N$: sulfur trioxide triethylamine;
TfOH: trifluoromethanesulfonic acid Hydrolysis 4,6-Di-O-phosphate-myo-inositol (2)

2-O-Tert-butyldimethylsilyl-1,3,5-orthoformate-4,6-(O-dixylylenephospho)-myo-inositol (1.00 g, 1.5 mmol, 1 eq.) in methanol/dichloromethane (MeOH/DCM) 30% (30 ml, 0.05 M) was treated with trimethylsilyl bromide (TMSBr) (11 ml, 83.8 mmol, 56 eq.) and stirred for 5 h. The reaction mixture was degased with $N_2$ and the HBr was neutralized with 1 M NaOH solution. After 1-2 h it was concentrated to dryness. The crude was washed twice with acetone and twice with acetonitrile (ACN) to give 2 as a white solid (539 mg, quantitative yield).

Sulfation 1,2,3,5-Tetra-O-sulfonyl-4,6-(di-O-phosphate)-myo-inositol (1)

4,6-di-O-phosphate-myo-inositol (30 mg, 90 μmol, 1 eq.) was co-evaporated with toluene (3×) and dried under high vacuum for 1 h. Dry dimethylformamide (DMF) (1 ml, 0.09 M) was added and the reaction mixture was treated with $SO_3$-$Et_3N$ (197 mg, 109 μmol, 12 eq.) and TfOH (190 μl, 215 μmol, 24 eq.). It was heated at 45° C. and stirred overnight. The reaction mixture was neutralized by addition of $Et_3N$ (0.15 ml, 12 eq.). Immediately after the neutralization the mixture was diluted in nanopure water (2 ml) and loaded on a sephadex G10 column. 14 fractions of 3-4 ml were collected and put into the freeze-dryer overnight. Fractions 3-7 were combined to give 1 as a white solid (46.31 μmol, 51%).

$^1$H-NMR (400 MHz, D$_2$O): δ (ppm)=5.40 (br, 1H, H—C2), 4.64-4.44 (m, 5H, H—C1/3, H—C5, H—C4/6), 3.70 (s, 8H, internal standard dioxane), 3.15 (q, J=7.3 Hz, 6H, CH2-Et$_3$N), 1.23 (t, J=7.3 Hz, 9H, CH3-Et$_3$N).

Synthesis of PEG-IP5 (III o, III p, III q)

The synthesis followed the sequence depicted in the scheme below:

DCM: dichloromethane;
DMF: dimethylformamide;
SBTO: tert-butyldimethylsilyl ether protection group;
TFA: trifluoroacetic acid;
mCPBA: meta-chloroperoxybenzoic acid Inositol orthoformate was reacted with 1 eq. of PEG tosylate to the singly PEG-ylated 4- or 6-PEG inositol orthoformate. The orthoformate protection group was removed using trifluoroacetic acid and dichloromethane. The compound was reacted with phosphoramidite, 1H-tetrazole, dichloromethane and meta-chloroperoxybenzoic acid. The resulting compound was reacted with H$_2$, MeOH and PdO to 4-PEG-IP5 or 6-PEG-IP5, respectively.

Synthesis of 4,6-PEG-IP4 (IV f, IV g, IV h)

The synthesis followed the sequence depicted in the scheme below:

DCM: dichloromethane;
DMF: dimethylformamide;
SBTO: tert-butyldimethylsilyl ether protection group;
TFA: trifluoroacetic acid;
mCPBA: meta-chloroperoxybenzoic acid

Inositol orthoformate was reacted with PEG tosylate to the doubly PEG-ylated 4,6-PEG inositol orthoformate. The orthoformate protection group was removed using trifluoroacetic acid and dichloromethane. The compound was reacted with phosphoramidite, 1H-tetrazole, dichloromethane and meta-chloroperoxybenzoic acid. The resulting compound was reacted with H$_2$, MeOH and PdO to 4,6-PEG-IP4

Synthesis of 4-PEG-IP2S3 (III u, III v, III w)

The synthesis followed the sequence depicted in the scheme below:

The known myo-inositol orthoformate can be mono alkylated with a commercial PEG tosylate in the presence of a strong based such as sodium hydride in DMF. The reaction mixture is then quenched with water and extracted with dichloromethane. The organic layer is dried and concentrated under reduced pressure. The product can be purified by silica gel chromatography. Phosphorylation of the free hydroxyl groups is done under standard conditions using a phosphoramidite reagent followed by oxidation with meta-chloroperbenzioc acid. The product can be purified by normal or reverse phase chromatography. The orthoester and phosphate groups are then deprotected concomitantly using excess bromotrimethylsilane in a mixture of methanol and dichloromethane. The product can be purified by precipitation or reverse phase chromatography. Sulfation of the free hydroxyl group is performed by suspending the product in dry DMF and reacting with excess sulfur trioxide-DMF complex. The reaction is then quenched with water and neutralized. The final product can be precipitated out of the reaction mixture by adding methanol and purified by size-exclusion chromatography or reverse phase chromatography.

Synthesis of PEG-IT5, 4,6-PEG-IT4 and PEG-IT2S3

The synthesis of PEG-IT5 (III r, III s, III t), 4,6-PEG-IT4 (IV i, IV j, IV k) and PEG-IT2S3 (III x, III y, III z) followed the sequences specified for PEGIP5, 4,6-PEG-IP4 and PEG-IP2S3, except that the phosphorylation was performed by addition of 1H tetrazole (4 eq.) followed by phosphoramidite (8 eq.) to the reaction and stirred overnight. Afterwards, pyridine, followed by crushed sulphur flakes (20 eq.) were added to the reaction and stirred overnight to complete the thiophosphorylation.

Synthesis of 2,4,6-PEG-IP3 (V d, V e, V f)

The synthesis followed the sequence depicted in the scheme below:

Inositol orthoformate was reacted with PEG tosylate to the triple PEG-ylated 2,4,6-PEG inositol orthoformate. The orthoformate protection group was removed using trifluoroacetic acid and dichloromethane. The compound was reacted with phosphoramidite, 1H-tetrazole, dichloromethane and meta-chloroperoxybenzoic acid. The resulting compound was reacted with $H_2$, MeOH and PdO to 2,4,6-PEG-IP4.

Synthesis of 2,4,6-PEG-IT3 (V g, V h, V i)

The synthesis of 2,4,6-PEG-IT3 followed that described for 2,4,6-PEG-IP3 except that the phosphorylation was performed by addition of 1H tetrazole (4 eq.) followed by phosphoramidite (8 eq.) to the reaction and stirred overnight. Afterwards, pyridine, followed by crushed sulphur flakes (20 eq.) were added to the reaction and stirred overnight to complete the thiophosphorylation.

The invention claimed is:

1. A method for treatment of a condition related to pathological calcium crystallization, comprising administering to a subject in need thereof a compound described by a general formula (II)

(II)

wherein
one or two or three X are $R^1$ and the remaining X independently from each other are selected from $OPO_3^{2-}$, $OPSO_2^{2-}$, and $OSO_3^-$; and
each $R^1$ independently of any other $R^1$ is a polyethylene glycol or a polyglycerola.

2. The method for treatment of a condition related to pathological calcium crystallization according to claim 1, wherein $R^1$ has a molar mass between 100 g/mol and 3000 g/mol.

3. The method for treatment of a condition related to pathological calcium crystallization according to claim 1, wherein the compound is characterized by a general formula III a, III b, III c or III d:

(III a)

(III b)

(III c)

(III d)

(III e)

(III f)

(III g)

(III h)

(III i)

(III j)

wherein each X (independently) and $R^1$ have the meaning outlined above.

4. The method for treatment of a condition related to pathological calcium crystallization according to claim 1, wherein more than one $R^1$ is present and each $R^1$ is the same as any other $R^1$.

5. The method for treatment of a condition related to pathological calcium crystallization according to claim 1, wherein the compound is characterized by a general formula (IV a), (IV b), (IV c), (IV d), (V a) or (V b)

(IV a)

(IV b)

(IV c)

(IV d)

-continued (V a)

(V b)

wherein each X (independently) and R¹ have the meaning outlined above.

6. The method for treatment of a condition related to pathological calcium crystallization according to claim 1, wherein one or two or three X are R¹ and the remaining X are
all $OPO_3^{2-}$ or
all $OPSO_2^{2-}$ or
all $OSO_3^{-}$.

7. The method for treatment of a condition related to pathological calcium crystallization according to claim 1, wherein
one or two or three X are R¹ and the remaining X are $OPO_3^{2-}$; and
R¹ is a polyethylene glycol and has a molar mass between 100 g/mol and 3000 g/mol.

8. The method for treatment of a condition related to pathological calcium crystallization according to claim 1, wherein
one or two or three X are R¹ and the remaining X are $OPSO_2^{2-}$; and
R¹ is a polyethylene glycol and has a molar mass between 100 g/mol and 3000 g/mol.

9. The method for treatment of a condition related to pathological calcium crystallization according to claim 1, wherein two X are R¹.

10. The method according to claim 1, wherein:
one X is R¹ and of the remaining X
three X are $OSO_3^{-}$ and two X are $OPSO_2^{2-}$, or three X are $OSO_3^{-}$ and two X are $OPO_3^{2-}$, and
R¹ is a polyethylene glycol and has a molar mass between 100 g/mol and 3000 g/mol.

11. The method for treatment of a condition related to pathological calcium crystallization according to claim 1, wherein R¹ is a polyethylene glycol characterized by a formula $R^3-(O-CH_2-CH_2)_n-$ or $R^3-(O-CH_2-CH_2)_n-O-$ and R³ is hydrogen, methyl or ethyl.

12. The method for treatment of a condition related to pathological calcium crystallization according to claim 1, wherein the compound is described by a general formula (III k), (III l), (III m), (III n), (IV e) or (V c)

(III k)

(III l)

(III m)

(III n)

(IV e)

(V c)

wherein n has a value from 2 to 200.

13. The method for treatment of a condition related to pathological calcium crystallization according to claim 1, wherein the compound is described by any one of formulae (III o), (III p), (III q), (III r), (III s), (III t), (III u), (III v), (III w), (III x), (III y), (III z), (IV f), (IV g), (IV h), (IV i), (IV j), (IV k), (V d), (V e), (V f), (V g), (V h) or (V i)

(III o)

(III p)

(III q)

-continued (V f)

(V g)

(V h)

(V i)

14. The method according to claim 1, wherein said polyethylene glycol is a monodisperse polyethylene glycol.

15. The method according to claim 1, wherein the compound is described by any one of formulae (III o), (III p), (III q), (III u), (III v) or (III w)

(III o)

(III p)

(III q)

(III u)

(III v)

(III w)

16. A compound described by a general formula (II)

(II)

wherein two X are $R^1$ and the remaining X independently from each other X are selected from $OPO_3^{2-}$, $OPSO_2^{2-}$, and $OSO_3^-$; and each $R^1$ independently of any other $R^1$ is a polyethylene glycol or a polyglycerol.

17. The compound according to claim 16, wherein the compound is described by any one of formulae (IV a)

(IV b)

(IV c)

-continued (IV d)

wherein each X (independently) and $R^1$ have the meaning outlined above.

18. The compound according to claim 16, described by the formula (IV e)

wherein n has a value from 2 to 200, particularly n is 2 or n is 7 to 50, more particularly n is 2, 7 to 12 or 40 to 50, even more particularly n is 2, 7, 9, 11 or 45.

19. The compound according to claim 16, described by any one of formulae (IV f)

(IV g)

(IV h)

(IV i)

(IV j)

-continued (IV k)

20. A compound described by any one of formulae (V d)

(V e)

(V f)

(V g)

(V h)

(V i)

* * * * *

UNITED STATES PATENT AND TRADEMARK OFFICE
CERTIFICATE OF CORRECTION

PATENT NO. : 10,624,909 B2
APPLICATION NO. : 16/060980
DATED : April 21, 2020
INVENTOR(S) : Mattias Ivarsson et al.

Page 1 of 1

It is certified that error appears in the above-identified patent and that said Letters Patent is hereby corrected as shown below:

In the Claims

Claim 1:
Column 27, Line 6, delete "polyglycerola", insert -- polyglycerol --

Claim 3:
Column 27, Line 14, delete "III c or III d:", insert -- III c, III d, III e, III f, III g, III h, III i, or III j: --

Claim 13:

Column 32, Line 5, delete " ", insert

-- 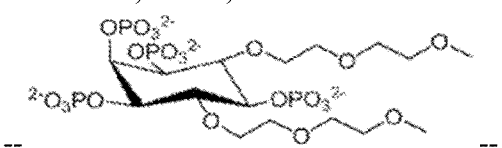 --

Signed and Sealed this
Second Day of August, 2022

Katherine Kelly Vidal
Director of the United States Patent and Trademark Office